US008170836B1

(12) United States Patent
Champaigne et al.

(10) Patent No.: US 8,170,836 B1
(45) Date of Patent: May 1, 2012

(54) LOW-POWER TRIGGERED DATA ACQUISITION SYSTEM AND METHOD

(75) Inventors: Kevin Champaigne, Conroe, TX (US); Jonathan Sumners, Conroe, TX (US)

(73) Assignee: Invocon, Inc., Conroe, TX (US)

( * ) Notice: Subject to any disclaimer, the term of this patent is extended or adjusted under 35 U.S.C. 154(b) by 521 days.

(21) Appl. No.: 12/362,504

(22) Filed: Jan. 30, 2009

Related U.S. Application Data

(60) Provisional application No. 61/026,129, filed on Feb. 4, 2008.

(51) Int. Cl.
*G06F 17/40* (2006.01)
(52) U.S. Cl. ............... 702/187; 702/35; 73/614; 73/588; 73/632; 73/587; 73/594; 345/177; 178/18.04
(58) Field of Classification Search .................... 702/35, 702/187; 73/583, 659, 587, 594; 345/177; 178/18.04; 367/13; 375/257, 219
See application file for complete search history.

(56) References Cited

U.S. PATENT DOCUMENTS

| 6,628,567 | B1 * | 9/2003 | Prosser et al. ................... 367/13 |
| 6,831,586 | B2 * | 12/2004 | Jansson .......................... 341/158 |
| 7,322,244 | B2 * | 1/2008 | Kim ................................. 73/587 |
| 7,450,023 | B2 * | 11/2008 | Muralidharan et al. ....... 340/665 |
| 7,562,576 | B2 * | 7/2009 | Fetzer et al. ..................... 73/614 |
| 7,643,015 | B2 * | 1/2010 | Paradiso et al. ................ 345/177 |
| 7,825,819 | B2 * | 11/2010 | Muralidharan et al. ....... 340/665 |
| 7,916,128 | B2 * | 3/2011 | Paradiso et al. ................ 345/177 |
| 2002/0012401 | A1 * | 1/2002 | Karolys et al. ................. 375/257 |
| 2003/0217873 | A1 * | 11/2003 | Paradiso et al. ............. 178/18.04 |
| 2006/0053075 | A1 * | 3/2006 | Roth et al. ....................... 705/50 |
| 2007/0182577 | A1 * | 8/2007 | Muralidharan et al. ....... 340/669 |
| 2009/0072964 | A1 * | 3/2009 | Muralidharan et al. ... 340/539.3 |
| 2010/0116563 | A1 * | 5/2010 | Paradiso et al. ............. 178/18.04 |

* cited by examiner

*Primary Examiner* — Carol Tsai

(74) *Attorney, Agent, or Firm* — Kenneth A. Roddy

(57) ABSTRACT

A low-power triggered data acquisition system and method utilizes low-powered circuitry, comparators, and digital logic incorporated into a miniaturized device interfaced with self-generating transducer sensor inputs to detect, identify and assess impact and damage to surfaces and structures wherein, upon the occurrence of a triggering event that produces a signal greater than a set threshold changes the comparator output and causes the system to acquire and store digital data representative of the incoming waveform on at least one triggered channel. The sensors may be disposed in an array to provide triangulation and location of the impact.

6 Claims, 1 Drawing Sheet

LOW-POWER TRIGGERED DATA ACQUISITION SYSTEM AND METHOD

CROSS REFERENCE TO RELATED APPLICATION

This application claims priority of U.S. Provisional Patent Application Ser. No. 61/026,129, filed Feb. 4, 2008.

STATEMENT REGARDING FEDERALLY SPONSORED RESEARCH OR DEVELOPMENT

This invention was made with Government support under Contract No. NNL06AA13C awarded by NASA. The Government has certain rights in the invention.

BACKGROUND OF THE INVENTION

1. Field of the Invention

This invention relates generally to monitoring and data acquisition devices and, more particularly to a low-power triggered data acquisition system and method utilizing low-powered circuitry and digital logic incorporated into a miniaturized device interfaced with self-generating transducer sensor inputs to detect, identify and assess impact and damage to surfaces and structures wherein, upon the occurrence of a triggering event that produces a signal greater than a set threshold causes the system to acquire and store digital data representative of an incoming waveform on at least one triggered channel.

2. Background Art

Prosser, et al, U.S. Pat. No. 6,628,567 discloses an acoustic monitoring device having at least two acoustic sensors with a triggering mechanism and a multiplexing circuit. After the occurrence of a triggering event at a sensor, the multiplexing circuit allows a recording component to record acoustic emissions at adjacent sensors. The acoustic monitoring device is attached to a solid medium to detect the occurrence of damage.

Devices for acquiring high-speed transient signals, for example acoustic emissions, typically require data acquisition electronics that are in a high-power mode for acquiring data on at least one channel at the full data acquisition rate. The power consumption of these high-speed data acquisition electronics is significantly high. To determine if the acquired data is a transitory event of interest, a digital circuit must process the acquired digital data in some way, which requires a significant amount of power and processor resources. Acquired data must be stored in digital memory temporarily while the data is processed, such that if a transient event of interest is detected, the acquired data can be obtained. Continuously storing data to memory requires a significant amount of power.

Continuous damage detection and characterization for various structures has been an elusive goal due to the transitory nature of the detectable high-frequency signals. A variety of techniques for detecting damage exist for using piezoelectric transducers to detect damage on aircraft, manned spacecraft, ships and underwater vehicles, motorized vehicles, storage tanks, pressure vessels, and civil structures. These techniques generally require the use of large numbers of piezoelectric sensor channels to be distributed throughout the structure to be monitored. Further, these sensors must be monitored continuously for transient signals that are indicative of damage, such as cracking, delamination, and impact. However, the size, complexity, and power consumption of the necessary electronics to acquire, process, and store the resulting digital waveforms is often too large to be included in operational vehicles or structures.

Various techniques have been used to monitor vehicles and structures for impact with micrometeoroids and orbital debris (MMOD) or other shock events in the past. Many involve the high-speed data acquisition and processing of large numbers of individual sensors, which are all wired back to a central location. Although capable of detecting events, the vehicle resources required for the systems, such as power, mass, and volume, have been excessive.

Invocon, Inc., of Conroe, Tex., also the owner of the present invention, has provided a wireless impact detection system to NASA for integration on the shuttle wing leading edges for the return to flight mission, and subsequent missions. The system records data from three channels of accelerometers at 20 k samples per second, performs post-processing algorithms to identify regions of raw launch data that may indicate an impact event, and then transmits only the processed data via RF through a wireless network to a laptop in the crew compartment. Although this system meets the requirements for monitoring the wing leading edges during launch, its ability to monitor throughout the entire mission for MMOD impacts is severely limited by battery power. Despite using the lowest power data acquisition and DSP electronics available, each unit's dual AA-cell battery pack can support only up to 10 hours of data acquisition and processing. The present system is a significant improvement over the earlier system.

SUMMARY OF THE INVENTION

The present invention overcomes the aforementioned problems, and is distinguished over the prior art in general, by a low-power triggered data acquisition system and method which utilizes low-powered circuitry, comparators, and digital logic interfaced with self-generating transducer inputs wherein, upon the occurrence of a triggering event that produces a signal greater than a set threshold changes the comparator output and causes the system to acquire and store digital data representative of the incoming waveform on at least one triggered channel. The system is incorporated into a miniaturized device which may be used to detect, identify and assess impact and damage to surfaces and structures. The system continuously monitors one or more piezoelectric transducers, such as accelerometers, acoustic emission sensors, or PZT elements for a transitory signal event, which is captured as a digital waveform with low latency. For continuous monitoring for transitory signals, a low-power circuit including analog circuitry, a comparator, and digital logic is interfaced to each self-generating transducer input. When a signal is produced which is greater than the threshold set on the comparator, the comparator output will change, causing the system to acquire and store digital data representative of the incoming waveform on the triggered channel, and other channels in the system. Data is recorded and the latch reset for the next event. Multiple channels of accelerometer, AE sensor, PZT element, or other self-generating transducer input may be provided to acquire the high-speed raw signal with low standby power and low latency. The sensors may be disposed in an array to provide triangulation and location of the impact.

One of the features and advantages of the present invention is that it utilizes low-power triggered data acquisition circuitry for continuous monitoring of spacecraft or other structures for accelerations or acoustic emissions caused by micrometeoroids and orbital debris (MMOD) or other shock events throughout all stages of a mission.

Another feature and advantage of the present invention is that consumes an extremely low amount of power and has the ability to monitor, acquire and process data for months or years for a long duration mission throughout all stages of the mission, such as moon or Mars exploration, without compromising the overall effective performance of the system.

Another feature and advantage of the present invention is that the distributed miniature sensor nodes minimize the expenditure of vehicle resources.

Another feature and advantage of the present invention is that it may be utilized to detect impacts on vehicles, such as the foam impact that caused the Space Shuttle Columbia tragedy or a micro-meteor impact on the International Space Station.

A further feature and advantage of the present invention is that it may be utilized as a general purpose hardware platform on which a wide variety of integrated structural health monitoring (ISHM) algorithms and sensing techniques can be implemented.

A further feature and advantage of the present invention is that it obtains relative time of arrival (TOA) information that will allow the determination of the arrival angle of the impact acceleration wave which is processed in a post-processing triangularization routine to provide information related to the location of the impact.

A still feature and advantage of the present invention is that it may incorporate configurable sample rates, sensor interfaces, actuation outputs, and local processing algorithms, to provide: active or passive modal-based damage detection, Lamb wave techniques for damage location, detection of leaks from pressurized vehicles and habitats through the produced airborne and surface-borne ultrasonic energy, and/or detection of crack propagation or delamination in structures through acoustic emission (AE) techniques.

Other features and advantages of the invention will become apparent from time to time throughout the specification and claims as hereinafter related.

DESCRIPTION OF THE PREFERRED EMBODIMENTS

Figure 1:
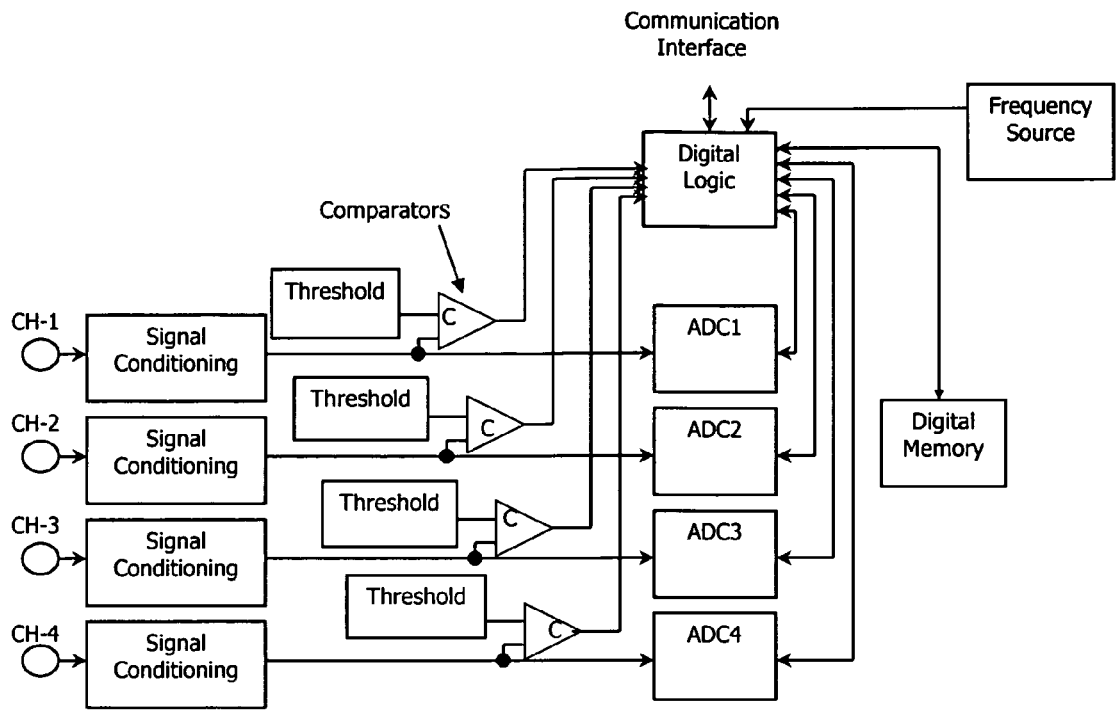
FIG. 1 is a schematic functional block diagram illustrating an example of a 4-channel system in accordance with the present invention.

Referring to the drawings by numerals of reference, there is shown in FIG. 1, a schematic functional block diagram illustrating an example of a 4-channel system in accordance with the present invention. In the illustrated example four channels CH-1, CH-2, CH-3, and CH-4 are shown, however, it should be understood that the present system could contain 1 or more channels, and two or more of the hardware blocks could be combined into a single integrated circuit.

Each channel has an impact sensor device which is a self-generating transducer, meaning that when the transducer is excited by the environment, it generates a voltage, current, or electrical charge output without requiring a constant excitation voltage or current. In other words, a charge signal can be generated without any power having to be supplied to the sensor element. Impact sensors or self-generating transducers suitable for use in the present system include, but are not limited to, piezoelectric-based transducers, including accelerometers, acoustic emission (AE) sensors, and PZT elements, pressure sensors, strain gauges, etc. Other options for the transducers include photo-transistors, photo-diodes, photo-cells, radiation detectors, and microphones, among others.

Each self-generating transducer sensor is interfaced with a comparator C that accepts two analog signals as inputs. A first input of the comparator receives the output of the self-generating transducer sensor and a known threshold voltage is applied to the second input of the comparator.

The output of the comparator is either low or high, depending upon whether the first input signal (from the self-generating transducer) is greater than second input signal (the threshold voltage) or not. In this way, as soon as the self-generating transducer sensor output goes higher than the known threshold voltage, the output of the comparator will change, thereby causing the system to acquire a block of data.

The threshold voltage may be either fixed or programmable and the value is set with either analog or digital components. For example, a resistor divider circuit may be used to set a fixed threshold value, and a digital potentiometer may be used as the programmable threshold source. The resistance value of the system is set by means of serial communication. This programmable resistance is used to divide the reference voltage down to the desired analog threshold value.

Each channel is provided with signal conditioning circuitry, and an analog-to-digital converter represented as ADC1, ADC2, ADC3, ADC4, since some amount of analog circuitry is required to properly condition the analog signals. Due to the high input impedance of the A/D converter and comparator, it is possible to implement only a passive filter and bias stage, which yields improved power consumption. For impacts capable of damaging a spacecraft, the signal would be strong enough and the transmission distance short enough that a signal buffer will not be necessary, but may be provided in other applications.

The analog-to-digital converter (ADC1 . . . ADC4) is preferably a high-speed, low-latency component that is capable of remaining in a low power state until a digital input causes it to begin sampling the analog input and providing digital output data.

A frequency source such as an RC oscillator provides the system clock function. A digital memory device is used to store the resulting digital data until it can be transferred to another device via a communication interface.

Digital logic circuitry is used to control the system operation including latching and reset, and to transfer data from the digital converters (ADC1 . . . ADC4) to the digital memory.

The low-power circuit interfaced to each self-generating transducer sensor continuously monitoring for impacts. When an acceleration signal is produced which is greater than the threshold set on the comparator, the comparator output will change. This event, along with the output from the other channels, will be recorded and the latch reset for the next event. Thus, the high-speed raw signal is acquired with an extremely low standby power circuit.

The acquisition of data on all channels in the system will begin within 1-2 sample periods, allowing nearly all of the triggering waveform to be captured, along with the complete signal waveform that arrives at one or more other channel inputs some time later.

Analog-to-digital converters are commercially available that allow all channels to begin acquiring simultaneous data at up to 2M samples per second approximately 2 µs after any of the four channels exceed the programmed threshold. However, since the frequency of interest is assumed to be on the order of 100 KHz, a much lower sample rate may be used for most applications, thereby saving significant power. Since the wave will likely arrive at each channel at various times, the other channels will often acquire the entire signal. This depends also on the wave propagation speed in the material.

A sensor array of at least four sensor elements provides reliable triggering and subsequent triangularization capabilities within a single unit. Thus, relative time of arrival (TOA) information is also be obtained that will allow the determination of the arrival angle of the acceleration "wave". The use of this angle in a post-processing triangularization routine provides information related to the location of the impact. Multiple units can be co-located and wired together to form systems with larger number of channels. Wireless communication may also be used to correlate data from multiple devices.

Figure 2:
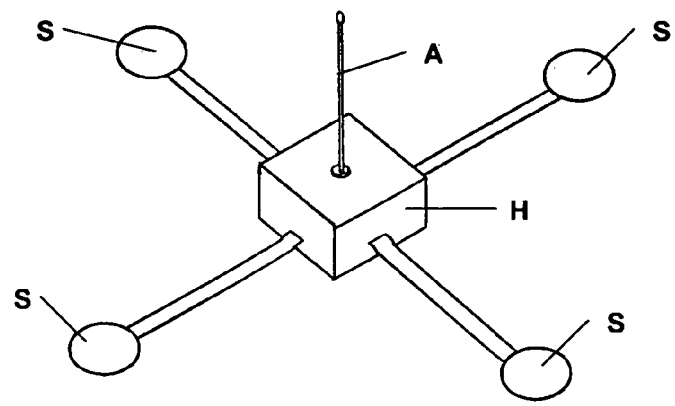
FIG. 2 is a perspective view illustrating an example of a miniaturized device incorporating a 4-channel system.

FIG. 2 shows an example of a miniaturized device incorporating a 4-channel system wherein the system circuitry is contained within a small housing H and interfaced with four self-generating transducer sensors S. An antenna A is connected with the digital memory in the housing for transferring digital data stored in memory to another device.

OPERATION

The basic operation of the low-power triggered circuit typically comprises the following actions:

(1) The threshold level is set, which is either a fixed setting or programmable by some means.

(2) The unit goes to a low-power trigger state.

(3) In the low-power trigger state, the device waits until the signal level on the comparator input is higher than the threshold setting, at which point the comparator output changes.

(4) The change in output of the comparator causes the digital logic to take the converter out of power down mode, start a signal conversion, and power up the rest of the digital circuitry.

(5) The digital logic acquires data from the A/D converters (ADC1 ... ADC4) and stores a predetermined number of data samples in the digital memory.

Further options for system operation:

(6) If desired, the unit will process the acquired data to assist in eliminating false alarms and preprocessing the data to reduce required communication bandwidth.

(7) If required, communications with other devices may accomplished to enable multiple devices to acquire synchronized data.

(8) Once the predetermined amount of data is taken, the unit sends out a communication message containing relevant data to a master control unit.

(9) The unit reenters trigger mode and the circuit is then ready for the next event.

Steps 1 through 4 occur in less than a few micro-seconds, which will allow for virtually 100% of the transient signal to be recorded. At any point, the system can awaken by itself at predetermined time to set the threshold of the digital potentiometer to a different level or receive other commands from the master control unit.

The present signal conditioning circuit design is capable of operation in the micro-watt range on average while constantly maintaining the capability to process and acquire very high-frequency acoustic signals. Such performance can provide operating lifetimes of 10+ years on a single AA battery, or unlimited operation from scavenged power sources. In addition, autonomous collaboration and synchronization between nodes of the network may provide for accurate location determination through amplitude and time-of-arrival analysis. Additionally, the system provides a general purpose hardware platform on which integrated structural health monitoring algorithms and sensing techniques can be implemented.

Mechanical waves travel at a maximum of about 6000 m/s. Sensors with a 2 micro-second response time would only need to be roughly 12 mm apart for the other channels in the system to acquire the entire digital waveform of interest. Particular applications may require wider sensor element spacing, yielding significant pre-trigger data capture.

In a wired system, wherein multiple units are co-located and wired together to form systems with larger number of channels, a trigger signal may be transmitted between units and synchronized data acquisitions with accuracies on the order of microseconds achieved, thereby creating an extensible system with a potential for an extremely large number of total channels. This trigger channel could also be used for external synchronization when available from other sources.

Although the present low-power triggered data acquisition system and method has been described, for purposes of example, as being implemented in a spacecraft system to provide MMOD impact characterization while in space, it should be understood that it may be implements in other spacecraft integrated structural health monitoring (ISHM) systems, for example, in inflatable/deployable crew habitats for lunar or Mars programs. This system may also include both passive detection as described, as well as active sensing applications, where a transducer is used to excite the structure and the present device would capture the resulting response.

The present low-power triggered data acquisition system and method may also be implemented in testing and evaluating various military weapons systems for high-speed triggered acquisition of impact data. Using light and/or sound sensitive sensors, the present low-power triggered data acquisition system and method may also be used for detecting and locating the source of gunfire.

The present low-power triggered data acquisition system and method may also be implemented in non-flight applications such as shipment environmental of critical cargo to provide a long term, battery-operated, shock, vibration, and temperature monitoring system for monitoring critical items during transport. Commercial systems exist which provide simple threshold detection, but the complete acquisition of shock or excessive vibration waveforms from a miniature battery operated device is not possible.

While the invention has been disclosed in various preferred forms, with respect to various specific examples and embodiments, the invention is not limited thereto. The specific embodiments thereof as disclosed and illustrated herein are considered as illustrative only of the principles of the invention and are not to be considered in a limiting sense in interpreting the claims. The claims are intended to include all novel and non-obvious combinations and sub-combinations of the various elements, features, functions, and/or properties disclosed herein.

Variations in size, materials, shape, form, function and manner of operation, assembly and use, are deemed readily apparent and obvious to one skilled in the art from this disclosure, and all equivalent relationships to those illustrated in the drawings and described in the specification are intended to be encompassed in the following claims defining the present invention.

The invention claimed is:

1. A low-power triggered data acquisition system for continuously monitoring detecting, identifying and assessing impact and damage to surfaces, comprising:

a plurality of self-generating transducer sensors that do not require constant excitation voltage or current disposed on the surface for generating an electrical charge output signal responsive to a triggering event;

a plurality of comparator means each having a first input interfaced with a respective said transducer sensor for receiving said electrical charge output signal from the respective said sensor, a second input for receiving a threshold voltage from a voltage source correlated with a respective sensor, and each comparator means having an output;

digital memory means for storing digital data;

digital logic circuitry interfaced with a frequency source functioning as a clock means and with said comparator means output for controlling the operation of the system including latching and reset functions, and transferring data from each said digital converter means to said digital memory means; and signal conditioning means and analog-to-digital converter means interfaced with said self-generating transducer sensors, said digital logic circuitry, and said first input of each said comparator means for conditioning analog output signals from said sensors prior to being received by each said comparator means;

wherein, the output of said comparator means changes upon receiving an electrical charge output signal from a first one of said sensors that is greater than the threshold voltage correlated with said first one of said sensors received by said comparator means to cause said digital logic circuitry to acquire and store digital data representative of a first triggering event generated by said first one of said sensors in said digital memory means, along with the output from the other said sensors, and said digital logic circuitry latches and resets the system for detecting a subsequent triggering event.

2. The low-power triggered data acquisition system according to claim 1, further comprising:

communication interface means coupled with said digital memory means for transferring digital data stored in said memory means to another device.

3. The low-power triggered data acquisition system according to claim 1, wherein said analog-to-digital converter means comprises a high-speed, low-latency component that is capable of remaining in a low power state until a digital input causes it to begin sampling analog input and providing digital output data.

4. The low-power triggered data acquisition system according to claim 1, wherein said self-generating transducer sensors are disposed on the surface in an array to provide triangulation, and said digital logic circuitry is programmed to perform a triangularization routine;

the triggering event is an impact on the surface and the digital data acquired is representative of an acceleration wave that arrives at one or more of said sensors at different times; and said digital logic circuitry, said clock means and said triangularization routine determine the arrival angle of the acceleration wave to provide data representing relative time of arrival at one or more of said sensors and thereby provide information related to the location of the impact.

5. The low-power triggered data acquisition system according to claim 1, wherein said frequency source comprises an RC oscillator.

6. The low-power triggered data acquisition system according to claim 1, wherein said self-generating transducer sensors are selected from the group consisting of impact sensors, piezoelectric-based transducers, accelerometers, acoustic emission (AE) sensors, PZT elements, pressure sensors, strain gauges, photo-transistors, photo-diodes, photo-cells, radiation detectors, and microphones.

* * * * *